(12) United States Patent
Trapani et al.

(10) Patent No.: US 9,445,956 B1
(45) Date of Patent: Sep. 20, 2016

(54) DRESSING APPLICATOR

(71) Applicants: Charles C. Trapani, Norfolk, VA (US);
E. Waightstill Avery, Norfolk, VA (US)

(72) Inventors: Charles C. Trapani, Norfolk, VA (US);
E. Waightstill Avery, Norfolk, VA (US)

( * ) Notice: Subject to any disclaimer, the term of this patent is extended or adjusted under 35 U.S.C. 154(b) by 295 days.

(21) Appl. No.: 14/295,638

(22) Filed: Jun. 4, 2014

Related U.S. Application Data

(60) Provisional application No. 61/830,681, filed on Jun. 4, 2013.

(51) Int. Cl.
*A61F 15/00* (2006.01)
*A61F 15/02* (2006.01)

(52) U.S. Cl.
CPC ........... *A61F 15/005* (2013.01); *A61F 15/001* (2013.01); *A61F 15/002* (2013.01); *A61F 15/02* (2013.01)

(58) Field of Classification Search
CPC .... A61F 15/00; A61F 15/001; A61F 15/002; A61F 15/003; A61F 15/005; A61F 15/007; A61F 15/02; A61F 13/00072; A61F 13/00085
USPC ........... 221/30, 36, 40–46, 56, 59, 135, 221; 221/270, 274
See application file for complete search history.

(56) References Cited

U.S. PATENT DOCUMENTS

| | | | |
|---|---|---|---|
| 3,530,494 A | 9/1970 | Baratta | |
| 3,686,055 A | 8/1972 | Hermann | |
| 4,560,087 A | 12/1985 | Sato et al. | |
| 4,624,733 A | 11/1986 | Hamisch, Jr. | |
| 4,915,227 A | 4/1990 | Johns | |
| 5,014,896 A | 5/1991 | Reitmeier et al. | |
| 5,065,894 A * | 11/1991 | Garland | A61F 15/002 221/25 |
| 5,511,689 A | 4/1996 | Frank | |
| 5,860,561 A * | 1/1999 | Saldana | A61F 15/001 221/197 |
| 5,934,504 A | 8/1999 | Elliott | |
| 6,213,343 B1 | 4/2001 | Damikolas | |
| 6,299,018 B1 | 10/2001 | Kimbrell | |
| 7,090,109 B2 | 8/2006 | Burlingame et al. | |
| 7,683,235 B2 | 3/2010 | Wendorf | |
| 7,775,205 B2 | 8/2010 | Edgerly | |
| 7,975,876 B2 | 7/2011 | Farmer et al. | |
| 8,722,962 B2 | 5/2014 | Dera et al. | |
| 2002/0170918 A1* | 11/2002 | Solovay | A61F 15/002 221/73 |
| 2006/0097002 A1 | 5/2006 | Chavez | |
| 2007/0191753 A1* | 8/2007 | Wendorf | A61F 15/002 602/58 |
| 2011/0017392 A1 | 1/2011 | Erives | |
| 2012/0152076 A1* | 6/2012 | Webb | A61F 15/002 83/203 |

* cited by examiner

*Primary Examiner* — Kari Petrik
(74) *Attorney, Agent, or Firm* — Shaddock Law Group, PC

(57) ABSTRACT

A dressing applicator that deposits a dressing pad and tape portion onto a surface. The dressing applicator comprises a lever-actuated mechanism that biases various arms in order to position and deposit the dressing pad and tape portion onto a surface.

19 Claims, 14 Drawing Sheets

DRESSING APPLICATOR

CROSS-REFERENCE TO RELATED APPLICATIONS

This patent application claims the benefit of U.S. Patent Application Ser. No. 61/830,681, filed Jun. 4, 2013, the entire disclosure of which is incorporated herein by reference.

STATEMENT REGARDING FEDERALLY SPONSORED RESEARCH OR DEVELOPMENT

Not Applicable.

REFERENCE TO SEQUENCE LISTING, A TABLE, OR A COMPUTER PROGRAM LISTING COMPACT DISC APPENDIX

Not Applicable.

NOTICE OF COPYRIGHTED MATERIAL

The disclosure of this patent document contains material that is subject to copyright protection. The copyright owner has no objection to the reproduction by anyone of the patent document or the patent disclosure, as it appears in the Patent and Trademark Office patent file or records, but otherwise reserves all copyright rights whatsoever. Unless otherwise noted, all trademarks and service marks identified herein are owned by the applicant.

BACKGROUND OF THE INVENTION

1. Field of the Invention

The present disclosure relates generally to the field of medical devices. More specifically, the present invention relates to dressing applicator to aid in the application of a dressing.

2. Description of Related Art

Typically, dressings are applied by hand to needle stick sites after blood draws or Intravenous (IV) therapy.

Various dressing dispensers are available. However, while these dispensers dispense dressings, they do not assist healthcare professional to apply the dressing to a needle stick site or a wound. Dressings must still be applied manually, which can expose a healthcare professional or other care provider to potentially hazardous biomedical materials.

Patients are often exposed to nonsterile procedures or products after the needle stick or blood draw. Ofttimes, healthcare professionals would use nonsterile tape and/or nonsterile dressing materials (such as cotton balls) when dressing the needle stick site. In many instances, healthcare professionals will ask a patient to assist in the dressing process by, for example, holding a cotton ball in place over a needle stick site, while the healthcare professional applies tape over the cotton ball. Even if the tape and cotton ball were initially sterile, allowing the patient to touch or handle the cotton ball potentially introduces germs, bacteria, microorganisms, dirt, etc. into the cotton ball and/or tape.

Unfortunately, universal protocols, procedures, or standards for applying a dressing to a needle stick or blood draw site do not exist. Thus, patients are left to potentially inconsistent local protocols and procedures or the chosen method of a particular healthcare provider.

Any discussion of documents, acts, materials, devices, articles, or the like, which has been included in the present specification is not to be taken as an admission that any or all of these matters form part of the prior art base or were common general knowledge in the field relevant to the present disclosure as it existed before the priority date of each claim of this application.

BRIEF SUMMARY OF THE INVENTION

The dressing applicator of the present invention dispenses the dressing and applies the dressing to the wound. Unlike known dispensers or methods, the dressing applicator of this invention applies pressure on top of the dressing to attach the dressing to the skin. Additionally, the dressing applicator applies the dressing in a manner that is more sanitary than applying a dressing by hand.

In various exemplary embodiments, the dressing applicator of the present invention is a handheld device that deposits a dressing pad and tape portion onto a surface, particularly a surface where constant pressure is required. The dressing applicator comprises a lever-actuated mechanism that biases various arms in order to position and deposit the dressing pad and tape portion onto a surface.

In certain nonlimiting embodiments, the dressing applicator comprises a frame comprising a substantially rigid portion of material having a substantially planar surface portion and including a driver attachment ring spaced apart from a roll attachment ring; a handle/magazine, wherein the handle/magazine is formed so as to allow one or more dressing pads to be at least partially contained within a cavity of the handle/magazine, wherein the handle/magazine includes an opening formed proximate a top end of the handle/magazine, which allows the dressing pads to be slidably removed from the cavity of the handle/magazine, and wherein a handle/magazine spring is positioned within the cavity of the handle/magazine so as to provide a spring biasing force to any dressing pad contained within the cavity of the handle/magazine, biasing the dressing pad toward the opening; a roller extending from the driver attachment ring; a cutting element extending from the driver attachment ring; a driver wheel, wherein the driver wheel gear is formed around an outer surface of the driver wheel, wherein the driver wheel is rotationally attached about an outer surface of the driver attachment ring, and wherein a driver arm extends from the driver wheel; a first arm, wherein the first arm comprises an elongate portion of material extending from a first end to a second end and having a substantially recurved shape, wherein the first arm includes an aperture formed therethrough, proximate a first end of the first arm, and wherein a first arm foot extends proximate a second end of the first arm; a second arm, wherein the second arm comprises an elongate portion of material extending from a first end to a second end and having a substantially arcuate shape, wherein the second arm includes an aperture formed therethrough, proximate a first end of the second arm, and wherein a second arm foot extends proximate a second end of the second arm; a swing arm, wherein the swing arm extends from a first end to a second end, wherein the swing arm includes an extension axle extending from a first side of the swing arm and a swing arm keyed axle extending from a second side of the swing arm, and wherein the extension axle is formed so as to be received within the aperture formed in the first arm and the aperture formed in the second arm and provide a pivot point for the first arm and the second arm, such that when the swing arm is rotated, a first arm and a second arm move from a retracted position to an extended position; a lever, wherein the lever comprises an elongate portion of material extending from a first end to a second end and having a longitudinal axis, wherein a lever axle extends perpendicular to the longitudinal axis of the lever and provides a point for the lever, such that the lever is pivotably between a fully extended position and a fully retracted position; a gear system, wherein the gear system, in response to rotation of the lever rotates the driver wheel gear and the swing arm; and a cover element that at least substantially covers various components of the gear system and provides cover element apertures to help maintain components of the gear system in place.

In certain nonlimiting embodiments, the present invention includes a method for applying and tape portion and a dressing pad to a surface including supplying an tape roll on the roll attachment ring; supplying at least one dressing pad in the cavity of the handle/magazine; rotating the lever so that the at least one dressing pad is applied to an tape portion of the tape roll; positioning the dressing pad above a desired application surface; continuing to rotate the lever such that the dressing pad makes contact with the desired application surface and the tape portion is released from the roller and cutting element; and continuing to rotate the lever such that the first arm foot and second arm foot apply pressure to exposed adhesive portions of the tape portion to adhere the tape portion to the desired application surface.

Accordingly, the presently disclosed invention provides a dressing applicator that provides for sterile application of a dressing.

The presently disclosed invention separately provides a dressing applicator that provides for application of a pressure dressing.

The presently disclosed invention separately provides a dressing applicator that can be used to apply constant pressure to a portion of tape and a dressing pad while covering a needle stick site of one.

The presently disclosed invention separately provides a dressing applicator that can be easily manipulated by a user.

The presently disclosed invention separately provides a dressing applicator that applies a dressing pad with a consistent length of tape.

The presently disclosed invention separately provides a dressing applicator that can be easily sterilized.

The presently disclosed invention separately provides specific procedure/protocol for dressing a site after a needle stick or blood draw.

These and other aspects, features, and advantages of the present invention are described in or are apparent from the following detailed description of the exemplary, non-limiting embodiments of the present invention and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

BRIEF DESCRIPTION OF THE SEVERAL VIEWS OF THE DRAWINGS

As required, detailed exemplary embodiments of the present invention are disclosed herein; however, it is to be understood that the disclosed embodiments are merely exemplary of the invention that may be embodied in various and alternative forms, within the scope of the present invention. The figures are not necessarily to scale; some features may be exaggerated or minimized to illustrate details of particular components. Therefore, specific structural and functional details disclosed herein are not to be interpreted as limiting, but merely as a basis for the claims and as a representative basis for teaching one skilled in the art to employ the present invention.

The exemplary embodiments of this invention will be described in detail, with reference to the following figures, wherein like reference numerals refer to like parts throughout the several views, and wherein.

DETAILED DESCRIPTION OF THE INVENTION

Figure 1:
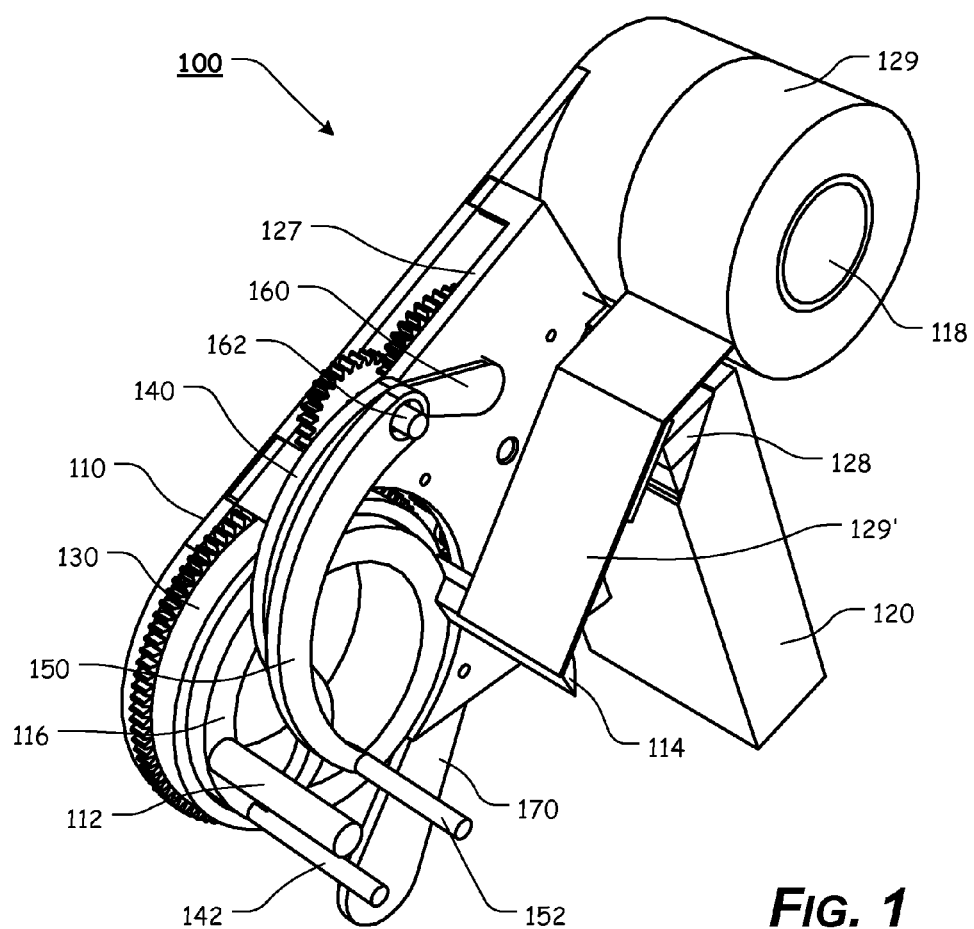
FIG. 1 illustrates a right side perspective view of a first exemplary embodiment of a dressing applicator, according to this invention.

For simplicity and clarification, the design factors and operating principles of the dressing applicator according to this invention are explained with reference to various exemplary embodiments of a dressing applicator according to this invention. The basic explanation of the design factors and operating principles of the dressing applicator is applicable for the understanding, design, and operation of the dressing applicator of this invention. It should be appreciated that the dressing applicator can be adapted to many applications where a dressing pad is to be applied, via an adhesive strip or tape, to a surface.

It should also be appreciated that the terms "dressing applicator", "dressing", "dressing pad", and "tape roll" are used for basic explanation and understanding of the operation of the systems, methods, and apparatuses of this invention. Therefore, the terms "dressing applicator", "dressing", "dressing pad", and "tape roll" are not to be construed as limiting the systems, methods, and apparatuses of this invention.

For simplicity and clarification, the systems and methods of this invention will be described as being used to apply a dressing to a needle stick site after blood draws or IV therapy. However, it should be appreciated that these are merely exemplary applications and uses of the systems and methods of the dressing applicator and are not to be construed as limiting this invention. Thus, the dressing applicator of this invention may be utilized in any application where it is desired to apply a dressing pad, via an adhesive strip or tape, to a surface.

Throughout this application the word "comprise", or variations such as "comprises" or "comprising" are used. It will be understood that these terms are meant to imply the inclusion of a stated element, integer, step, or group of elements, integers, or steps, but not the exclusion of any other element, integer, step, or group of elements, integers, or steps.

Turning now to the drawing FIGS., FIGS. 1-13 illustrate certain elements and/or aspects of a first exemplary embodiment of the dressing applicator 100, according to this invention. In illustrative, non-limiting embodiment(s) of this invention, as illustrated in FIGS. 1-13, the dressing applicator 100 comprise at least some of a frame 110, a handle/magazine 120, a driver wheel 130, a first arm 140, a second arm 150, a swing arm 160, a lever 170, and a gear system.

Figure 2:
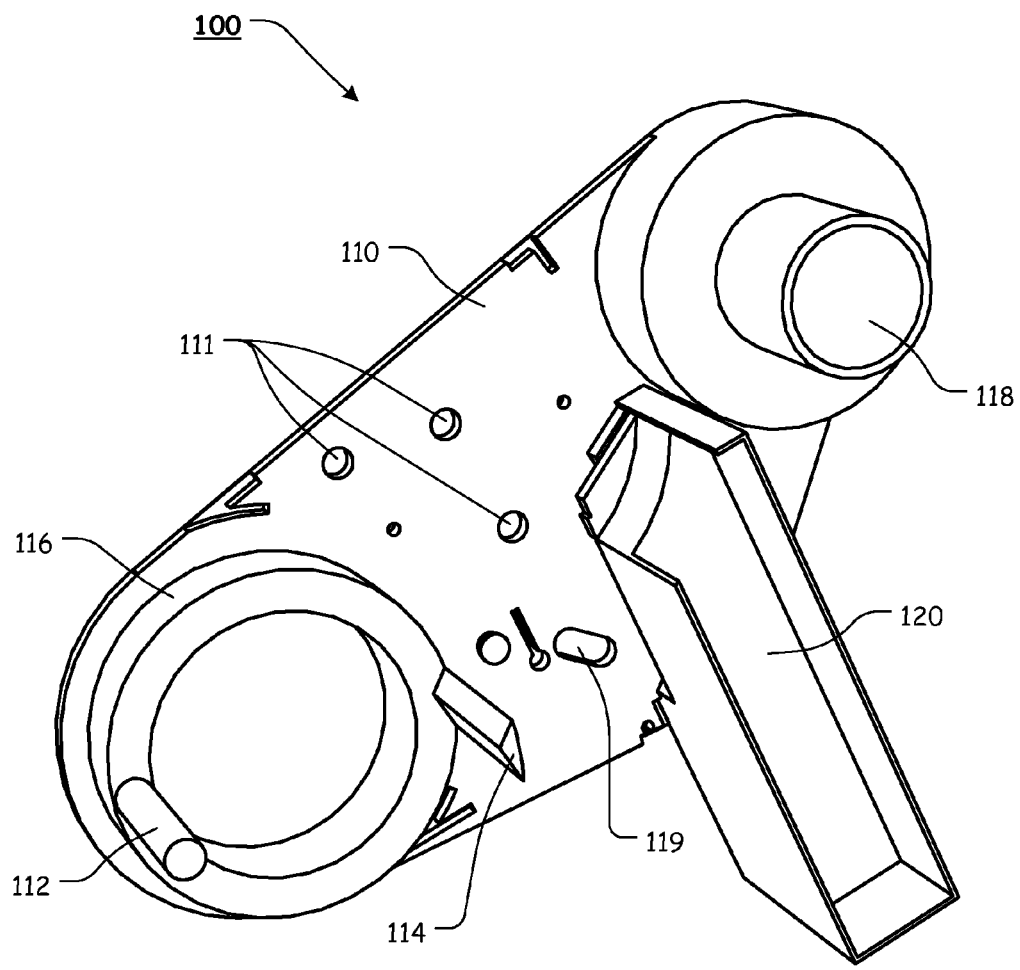
FIG. 2 illustrates a right side perspective view of a first exemplary embodiment of a frame for a dressing applicator, according to this invention.

In various exemplary embodiments, as illustrated most clearly in FIG. 2, the frame 110 comprises a substantially rigid portion of material having a substantially planar surface portion and including a driver attachment ring 116 spaced apart from a roll attachment ring 118. The driver attachment ring 116 and the roll attachment ring 118 both extend outwardly, substantially perpendicularly, from the planar portion of the frame 110.

The driver attachment ring 116 is shaped so as to allow the driver wheel 130 to be rotationally attached about an outer surface of the driver attachment ring 116. A substantially cylindrically shaped roller 112 extends from the driver attachment ring 116. In various exemplary embodiments, a longitudinal axis of the roller 112 extends perpendicular to the planar surface of the frame 110.

A cutting element 114 such as, for example, a razor, also extends from the driver attachment ring 116. In various exemplary embodiments, a longitudinal axis of the cutting element 114 extends perpendicular to the planar surface of the frame 110.

In certain embodiments, the roller 112 and the cutting element 114 are positioned at opposing sides of the driver attachment ring 116.

The roll attachment ring 118 is shaped so as to allow an tape roll 129 (such as, for example, a roll of tape) to be rotationally attached about an outer surface of the roll attachment ring 118. In certain exemplary embodiments, the roll attachment ring 118 extends directly from the planar surface of the frame 110. Alternatively, the roll attachment ring 118 may be spaced apart from the planar surface of the frame 110.

It should be appreciated that the tape roll 129 preferably comprises a sterile role of adhesive or non-adhesive tape, which is capable of adhering to at least a portion of a dressing pad 128 (as further described herein) and a desired surface, such as, for example, a patient's skin.

The handle/magazine 120 is formed so as to allow one or more dressing pads 128 to be at least partially contained within a cavity of the handle/magazine 120. The handle/magazine 120 includes an opening formed proximate a top end of the handle/magazine 120, which allows the dressing pads 120 to be slidably removed, one at a time, from the cavity of the handle/magazine 120. A handle/magazine spring 125 is positioned within the cavity of the handle/magazine 120 so as to provide a spring biasing force to any dressing pad 128 contained within the cavity of the handle/magazine 120, biasing the dressing pad 128 toward the opening.

In certain exemplary embodiments, the handle/magazine 120 optionally includes an ergonomic exterior shape and/or a knurled or textured portion. If included, these features assist the user in establishing a more secure grip or purchase on the handle/magazine 120.

In various exemplary embodiments, the dressing pads 128 comprise foam, gauze, cotton, or other single or composite materials. At least a portion of the dressing pads 128 may be impregnated or coated with an antibacterial, hydrochloride, or other substance to aid in the killing of bacteria or the healing process. It should be appreciated that the dressing pads 128 are preferably sterile when utilized in conjunction with the dressing applicator 100.

Figure 3:
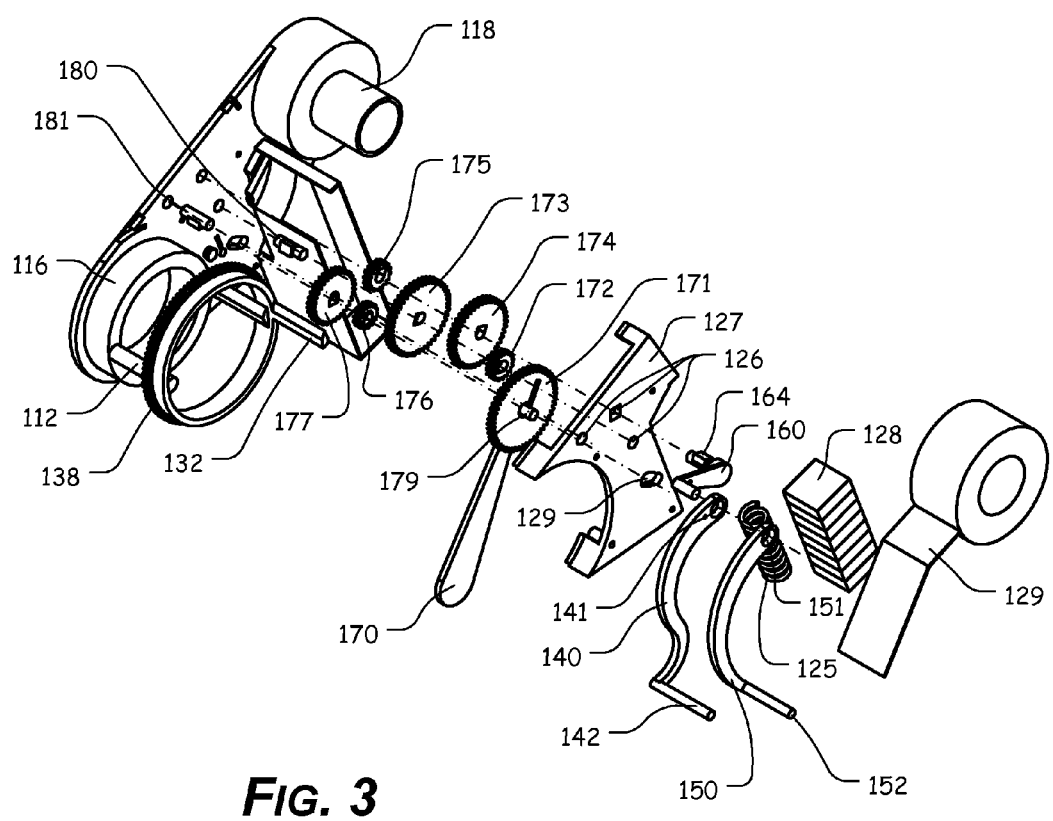
FIG. 3 illustrates an exploded perspective view of a first exemplary embodiment of a frame for a dressing applicator, according to this invention.
Figure 4:
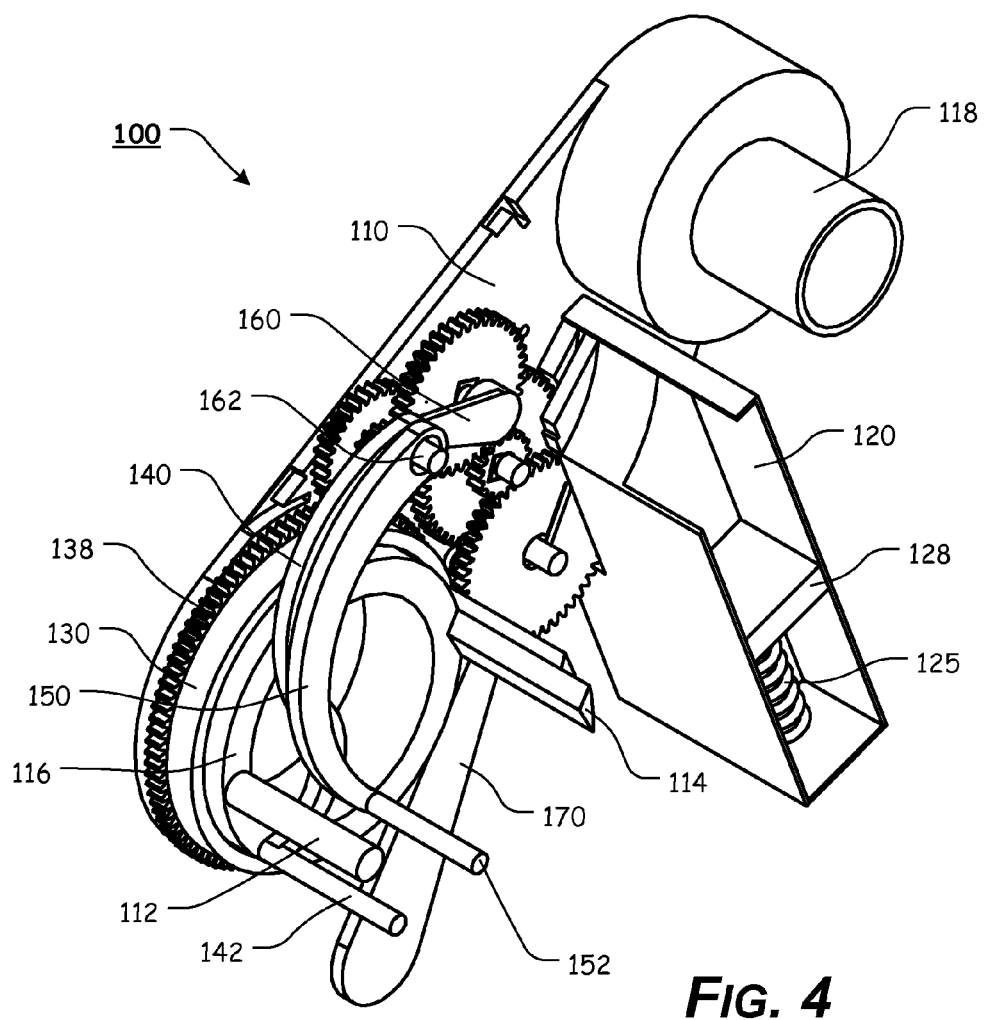
FIG. 4 illustrates a right side perspective view of a first exemplary embodiment of a dressing applicator according to this invention, wherein the cover element is removed to illustrate the gear system in greater detail.
Figure 5:
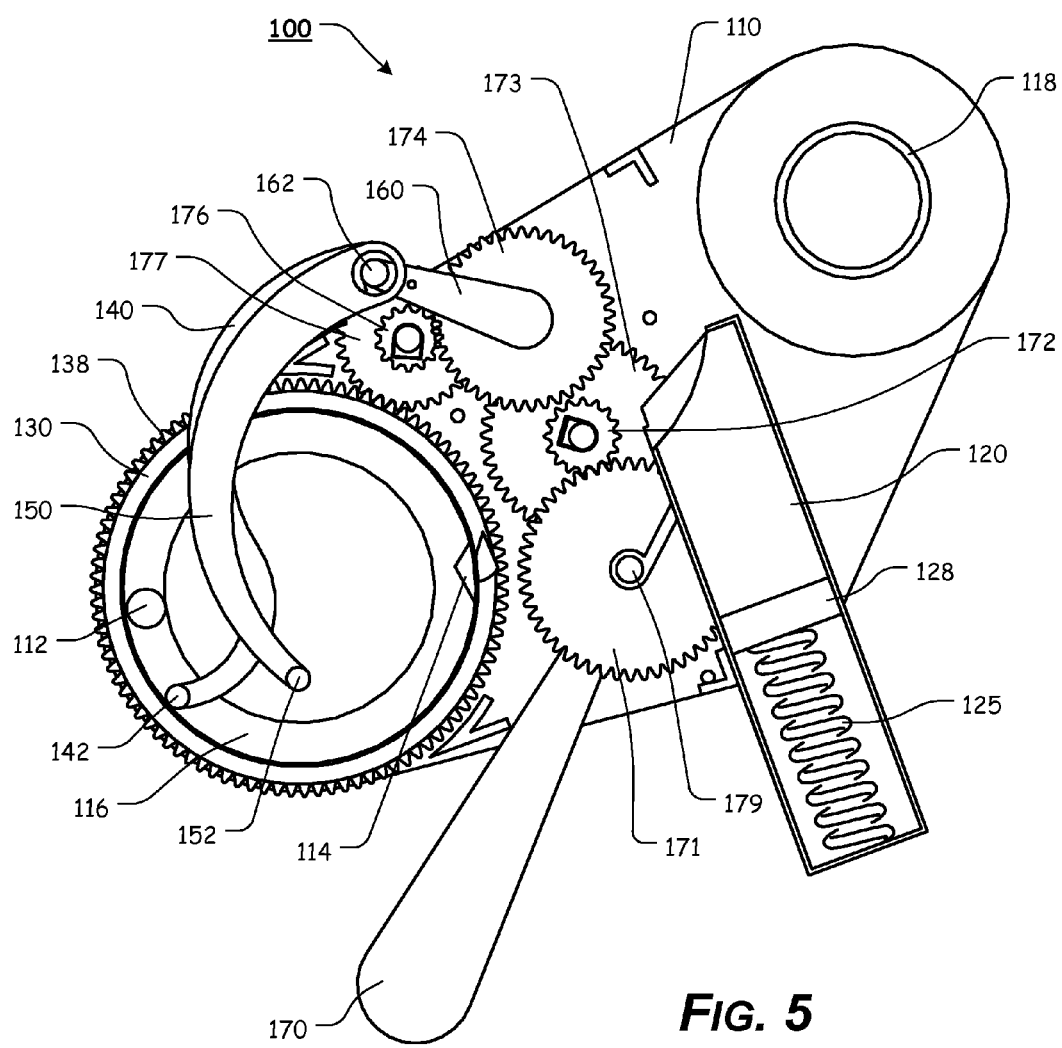
FIG. 5 illustrates a right side view of a first exemplary embodiment of a dressing applicator according to this invention, wherein the cover element is removed to illustrate the gear system in greater detail.
Figure 6:
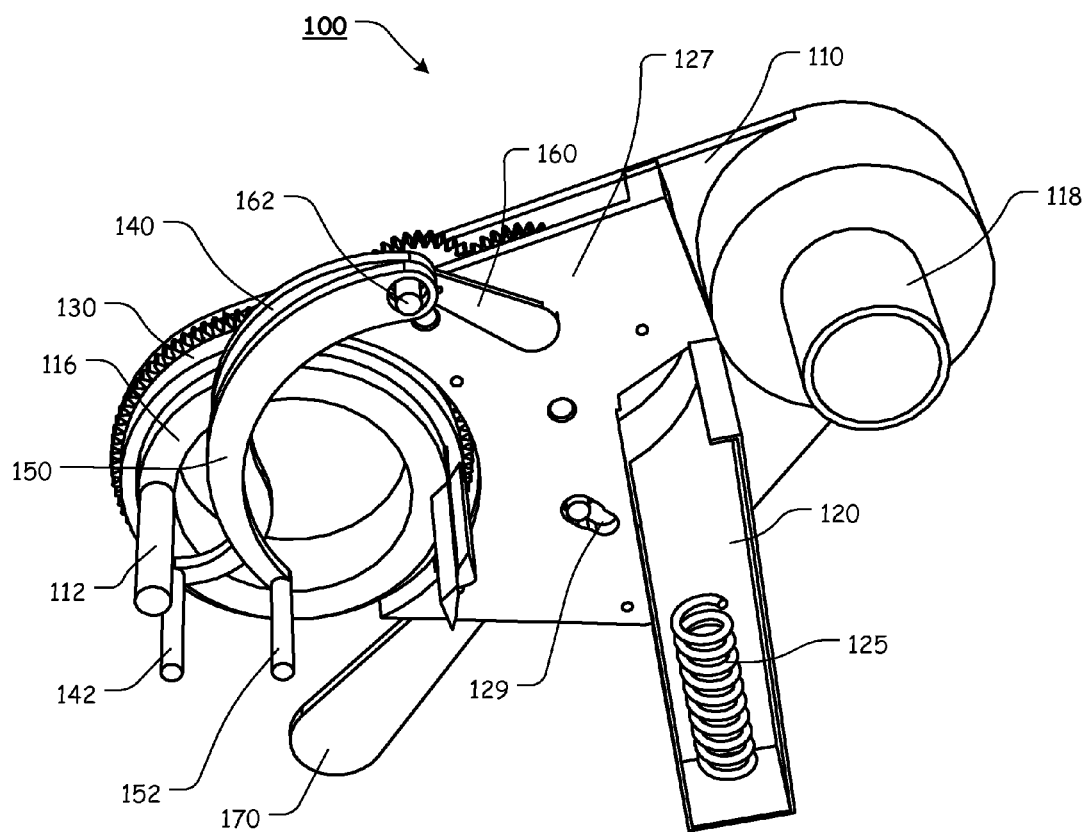
FIG. 6 illustrates an additional perspective view of a first exemplary embodiment of a dressing applicator according to this invention, wherein the tape roll and the dressing pads are removed.
Figure 7:
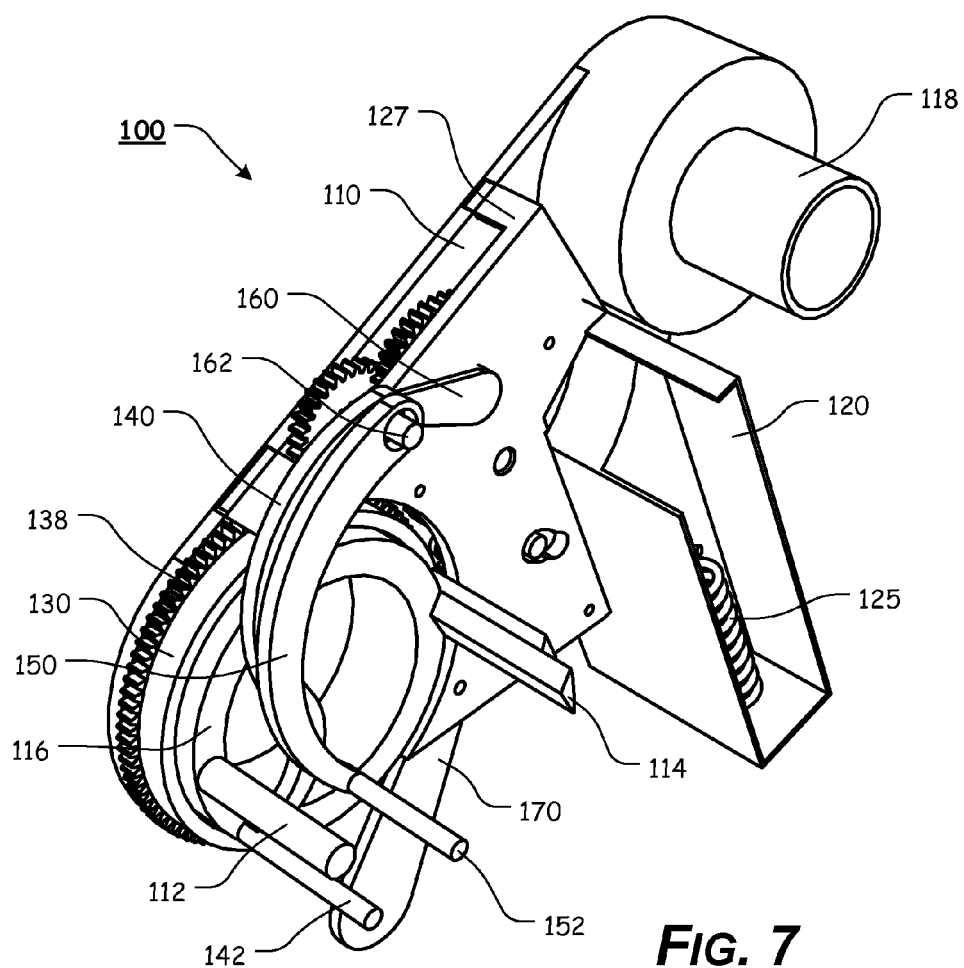
FIG. 7 illustrates an supplementary perspective view of a first exemplary embodiment of a dressing applicator according to this invention, wherein the tape roll and the dressing pads are removed.
Figure 8:
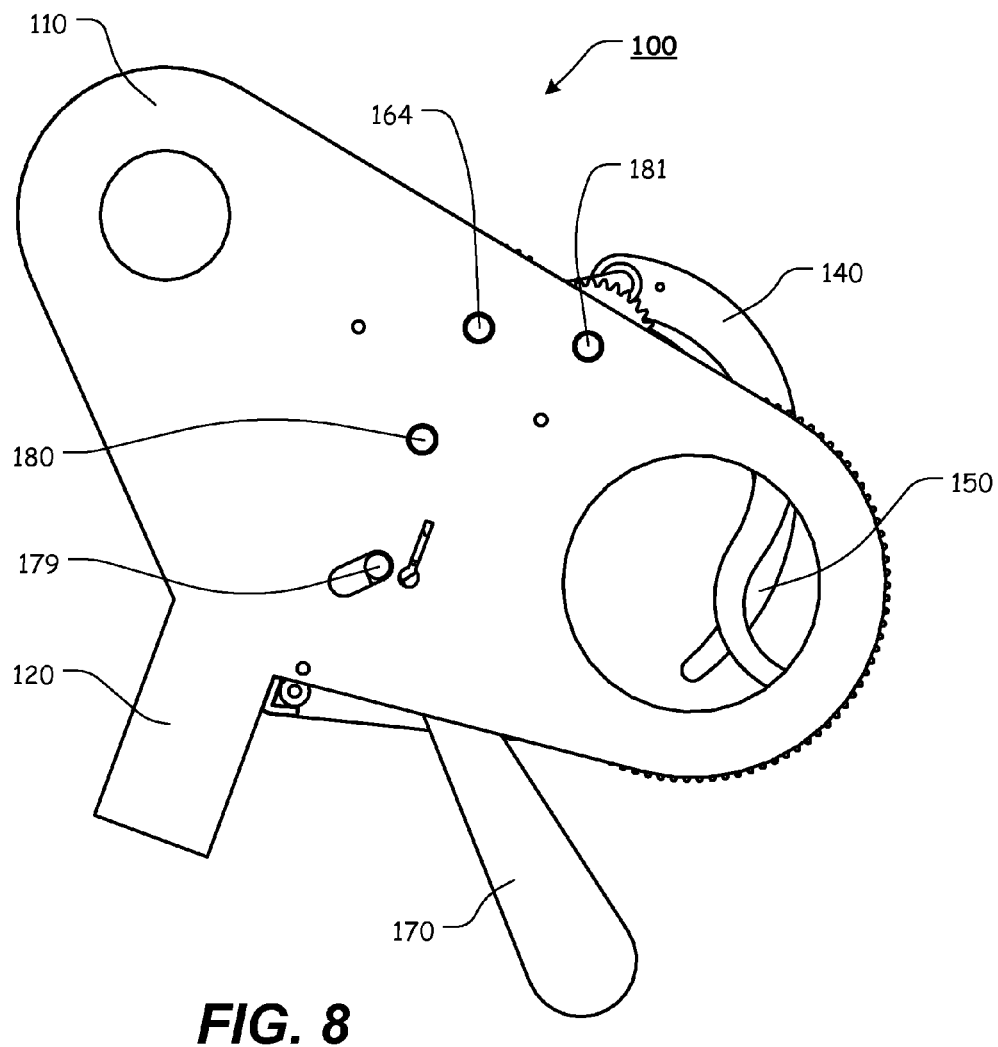
FIG. 8 illustrates a left side view of a first exemplary embodiment of a dressing applicator according to this invention.

While the dressing pads 128 may optionally be provided as individual, sterile dressing pads 128, it is preferred that the dressing pads 128 be provided in a prepackaged, cartridge form, as most clearly illustrated in FIG. 3. When provided in a prepackaged form, the sterile integrity of the individual dressing pads 128 can be more easily maintained. Additionally, the cartridge form allows the dressing pads 128 to be more easily inserted into the cavity of the handle/magazine 120.

In certain exemplary embodiments, the packaging used to package the dressing pads 128 may be removed prior to insertion of the dressing pad cartridge into the cavity. Alternatively, the dressing pad cartridge may be inserted, in its entirety, into the cavity of the handle/magazine 120, where a blade or other removal device automatically removes or opens the packaging prior to the first dressing pad 128 being attached to a portion of tape 129'.

In certain exemplary embodiments, the dressing pads 128 are contained within a self-contained cartridge that can be inserted into either a top, a bottom, or a side opening in the handle/magazine 120. In these embodiments, the cartridge may optionally contain a spring biasing element, such as, for example, handle/magazine spring 125.

The driver wheel 130 comprises a substantially circular ring having a central aperture formed therethrough. The central aperture is formed so as to receive at least a portion of the driver attachment ring 116 therein. In various exemplary embodiments, once positioned about the driver attachment ring 116, the driver wheel 130 is snap-fit or frictionally maintained so as to rotate about the driver attachment ring 116 while being maintained in a determined position relative to the driver attachment ring 116.

A driver wheel gear 138 is formed around an outer surface of the driver wheel 130.

A driver arm 132 extends from the driver wheel 130. In various exemplary embodiments, the driver arm 132 extends from the driver wheel 130 so as to interact with the cutting element 114 when the driver wheel 130 is positioned about the driver attachment ring 116.

The first arm 140 comprises an elongate portion of material extending from a first end to a second end and having a substantially recurved or "S" shape. The first arm 140 includes an aperture 141 formed therethrough, positioned proximate a first end of the first arm 140. A substantially cylindrically shaped foot 142 extends proximate a second end of the first arm 140. In various exemplary embodiments, a longitudinal axis of the foot 142 extends perpendicular to the longitudinal axis of the first arm 140.

The second arm 150 comprises an elongate portion of material extending from a first end to a second end and having a substantially arced or arcuate shape. The second arm 150 includes an aperture 151 formed therethrough, positioned proximate a first end of the second arm 150. A substantially cylindrically shaped foot 152 extends proximate a second end of the second arm 150. In various exemplary embodiments, a longitudinal axis of the foot 152 extends perpendicular to the longitudinal axis of the second arm 150.

The swing arm 160 extends from a first end to a second end. A swing arm 160 includes an extension axle 162 extending from a first side of the swing arm 160 and a keyed axle 164 extending from a second side of the swing arm 160. The extension axle 162 is formed so as to be received within the aperture 141 formed in the first arm 140 and the aperture 151 formed in the second arm 150 and provide a pivot point for the first arm 140 and the second arm 150.

Figure 9:
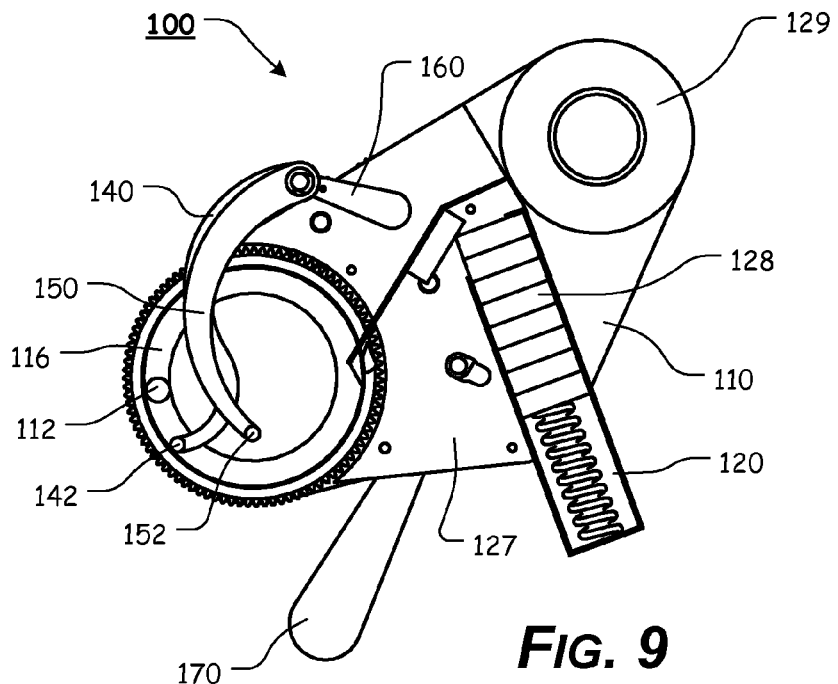
FIG. 9 illustrates a right side view of a first exemplary embodiment of a dressing applicator according to this invention, wherein the dressing applicator arms are in an initial, fully retracted, position.
Figure 13:
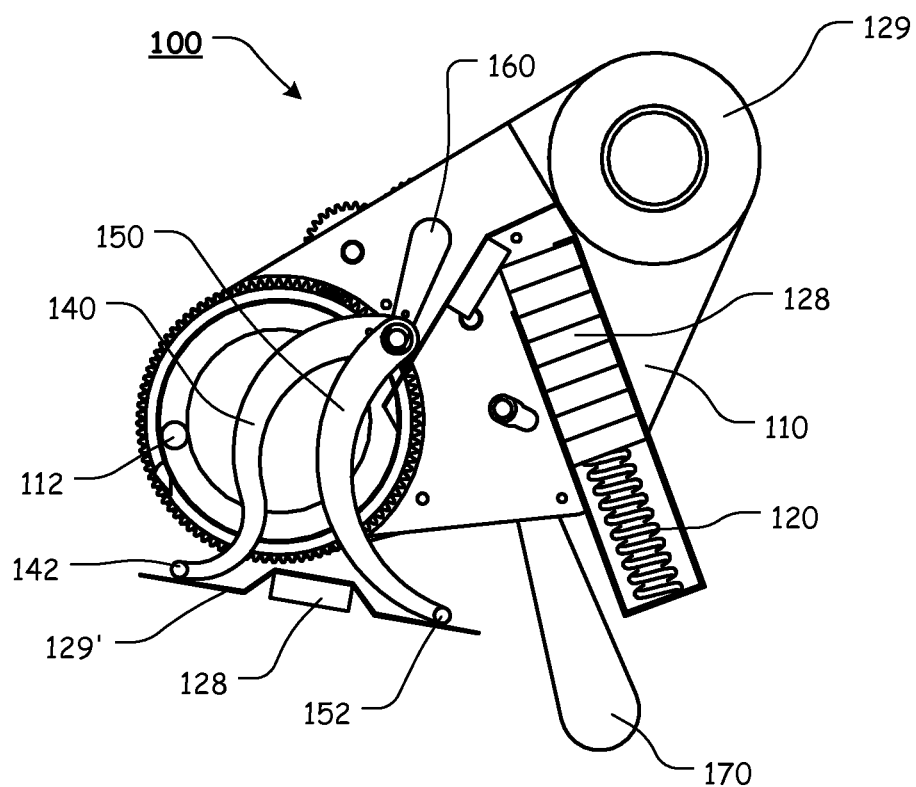
FIG. 13 illustrates a right side view of a first exemplary embodiment of a dressing applicator according to this invention, wherein the dressing applicator arms are in a fifth, fully extended, position.

In various exemplary embodiments, the lever 170 comprises an elongate portion of material extending from a first end to a second end and having a longitudinal axis. In certain exemplary embodiments, the lever 170 optionally includes an ergonomic design and/or a knurled or textured portion, which allows the user to establish a more secure grip or purchase on the lever 170. A lever axle 179 extends perpendicular to the longitudinal axis of the lever 170 and provides a point for the lever 170. The lever 170 is pivotably between an initial, fully extended position, as illustrated in FIG. 9 and a fully retracted position, as illustrated in FIG. 13.

A gear 171 is centered on the axle 179 and attached or coupled to the upper 170, such that when the lever 170 is rotated about the axle 179, the gear 171 rotates in angular alignment with the lever 170.

In various exemplary embodiments, the gear system comprises at least some of a gear 171, a gear 172, a gear 173, a gear 174, a gear 175, a gear 176, and a gear 177. As illustrated, the gears are aligned and maintaining in position by interaction of keyed axle 164, axle 179, keyed axle 180, and keyed axle 181 with certain frame apertures 111 and cover element apertures 126. For example, gears 174 and 175 are aligned with the keyed axle 164, gears 172 and 173 are aligned with keyed axle 180, and gears 176 and 177 are aligned with keyed axle 181. Furthermore, the axle 179 of the lever 170 is aligned with the disengage slot formed by disengage slot 119 and disengage slot 129.

Gear 171 is attached to the pivot point of the lever 170, which interfaces the lever 170 with the gear system. The gear system serves to increase the rotational input from the lever 170 to 360 degrees at the swing arm 160 and at the driver wheel 130. The gear system outputs to the driver wheel gear 138 and the swing arm 160.

The cover element 127 covers or substantially covers the various components of the gear system and/or provides cover element apertures 126 to help maintain components of the gear system in place.

In various exemplary embodiments, various components of the dressing applicator 100 are substantially rigid and are formed of plastic. Alternate materials of construction of the various components of the dressing applicator 100 may include one or more of the following: wood, steel, stainless steel, aluminum, titanium, and/or other metals, as well as various alloys and composites thereof, glass-hardened polymers, polymeric composites, polymer or fiber reinforced metals, carbon fiber or glass fiber composites, continuous fibers in combination with thermoset and thermoplastic resins, chopped glass or carbon fibers used for injection molding compounds, laminate glass or carbon fiber, epoxy laminates, woven glass fiber laminates, impregnate fibers, polyester resins, epoxy resins, phenolic resins, polyimide resins, cyanate resins, high-strength plastics, nylon, glass, or polymer fiber reinforced plastics, thermoform and/or thermoset materials, and/or various combinations of the foregoing. Thus, it should be understood that the material or materials used to form the various components of the dressing applicator 100 is a design choice based on the desired appearance and functionality of the dressing applicator 100.

It should be appreciated that certain elements of the dressing applicator 100 may be formed as an integral unit (such as, for example, the frame 110 and the handle/magazine 120). Alternatively, suitable materials can be used and sections or elements made independently and attached or coupled together, such as by adhesives, welding, screws, rivets, pins, or other fasteners, to form the various elements of the dressing applicator 100.

It should also be understood that the overall size and shape of the dressing applicator 100, and the various portions thereof, is a design choice based upon the desired functionality and/or appearance of the dressing applicator 100.

During operation of the dressing applicator 100, dressing pads 128 are placed within the cavity of the handle/magazine 120 and an tape roll 129 is placed on the roll attachment ring 118. As illustrated in FIG. 9, and initial portion of tape 129' is manually pulled from the tape roll 129, across a top dressing pad 128, such that the top dressing pad 128 is adhered to a center portion of the tape, and an end of the tape portion 129' is adhesively attached atop the cutting element 114.

When the dressing applicator 100 has been initially staged, as illustrated in FIG. 9, the lever 170 can then be rotated from the fully extended position to the retracted position to dispense a dressing. To rotate the lever 170, the lever is typically pulled by a user's fingers while the palm of the users same hand holds the handle/magazine 120.

Figure 10:
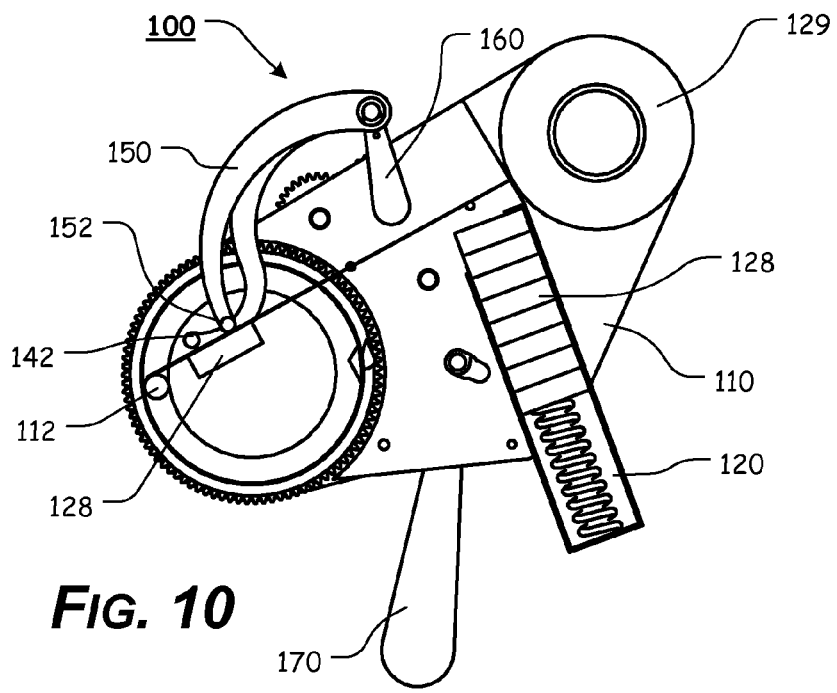
FIG. 10 illustrates a right side view of a first exemplary embodiment of a dressing applicator according to this invention, wherein the dressing applicator is in a second position.

As illustrated in FIG. 10, as the lever 170 is rotated/pulled from the initial, extended position, the first arm 140 temporarily adheres to the initial tape portion 129' and pulls the initial tape portion 129' for approximately 180 degrees of rotation until the tape portion 129' is temporarily adhered to and stopped by the roller 112. The swing arm 160 is simultaneously rotated, positioning the foot 142 and the foot 152 on the non-adhesive side of the tape portion 129', over the dressing pad 128.

Figure 11:
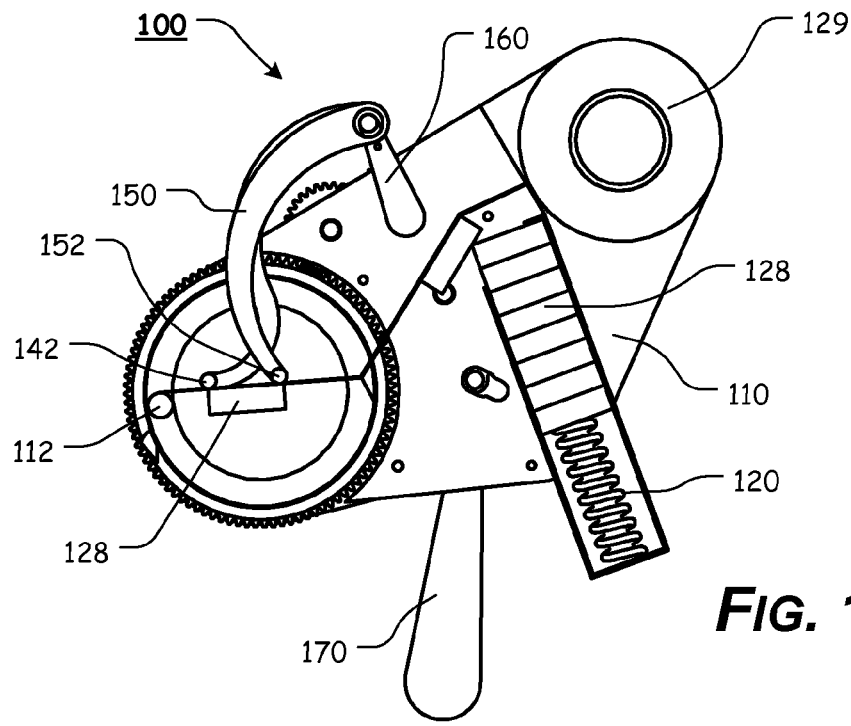
FIG. 11 illustrates a right side view of a first exemplary embodiment of a dressing applicator according to this invention, wherein the dressing applicator is in a third position.

Then, as illustrated in FIG. 11, as the lever 170 continues to be pulled, the first arm 140 releases from the tape portion 129' as the tape portion 129' is stopped by to roller 112. The swing arm 160 continues to rotate, driving the first arm 140 and the second arm 150 to push the tape portion 129' and dressing pad 128 downward, such that the tape portion 129' makes contact with the cutting element 114. As this occurs, a second tape portion 129' simultaneously adheres to the next dressing pad 128 from the handle/magazine 120 and slides the dressing pad 128 from the cavity of the handle/magazine 120 as the initial tape portion 129' is pushed down by the first arm 140 and the second arm 150.

Figure 12:
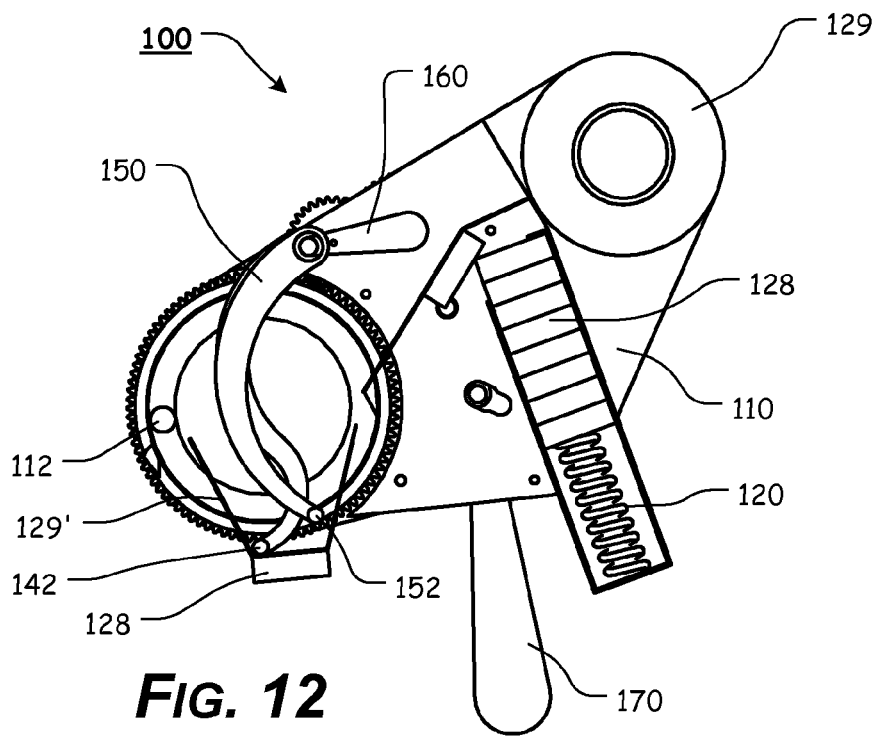
FIG. 12 illustrates a right side view of a first exemplary embodiment of a dressing applicator according to this invention, wherein the dressing applicator is in a fourth position.

Then, as illustrated in FIG. 12, the lever 170 continues to be pulled and the first arm 140 continues to rotate. The swing arm 160 continues to rotate, driving the first arm 140 and the second arm 150 into the initial tape portion 129' and forcing the initial tape portion 129' to be cut to the determined length by the cutting element 114. The initial tape portion 129' simultaneously begins to unroll from the roller 112.

Next, as illustrated in FIG. 13, the lever 170 continues to be pulled and the first arm 140 continues to rotate. The swing arm 160 continues to rotate, driving the first arm 140 and the second arm 150 further into the tape portion 129' and forcing the tape portion 129' and dressing pad 128 onto a desired surface. As pressure is exerted from the handle/magazine 120, forcing the first arm 140 and the second arm 150 onto the surface, the foot 142 and the foot 152 compress the dressing pad 128. When the appropriate pressure is exerted, the first arm 140 and the second arm 150 spread in order to secure the tape portion 129', while maintaining tension in the tape portion 129' to produce constant pressure when fully deposited.

It should be appreciated that the amount of pressure required to spread the first arm 140 and the second arm 150 may optionally be determined by a torsion spring or other resilient material (not shown) secured between the first arm 140 and the second arm 150. Another torsion spring or other resilient material (not shown) may optionally be secured between the first arm 140, the second arm 150, and the swing arm 160 at the desired angle. This angle corresponds to first arm 140 and second arm 150 guides built into the body of the device.

When the lever 170 is fully rotated to the retracted position, a spring-biased button (not shown) is released. As the lever 170 is released, a torsion spring or other resilient material (not shown) may optionally bias or rebound the lever 170 back towards the initial, extended position. As the lever 170 is returned to the initial, extended position, gear 171 is forced to disengage from gear 172 by the spring loaded button (not shown) that will be depressed during the pull and was released when the lever 170 was fully pulled.

Full "disengagement" is accomplished through a ramp-like geometry on the underside of the lever 170. The button (not shown) catches on the high end of the ramp when the lever 170 is fully pulled and forces the axle 179 of the lever 170 and gear 171 along the disengage slot formed by disengage slot 119 and disengage slot 129. When axle 179 is urged an appropriate distance, the spring loaded button (not shown) will pass the high ramp geometry and slip back to the low end. A tension spring (not shown) urges the axle 179 back to the reengaged position.

To use the dressing applicator 100 to apply the tape portion 129' and dressing pad 128 to a patient or another desired surface, the dressing applicator 100 is supplied with an tape roll 129 and at least one dressing pad 128. Just prior to or immediately after a needle is removed from a needle stick site after a blood draw or IV stick site after IV therapy, the lever 170 is rotated so that the dressing pad 128 is applied to the tape portion 129' and the first arm 140 and second arm 150 are positioned approximately as illustrated in FIG. 11. Then, the dressing pad 128 is positioned above the needle stick site and the lever 170 is rotated further such that the dressing pad 128 makes contact with the surface of the patient's skin and the tape portion 129' is released from the roller 112 and cutting element 114, approximately as illustrated in FIG. 12.

Once the dressing pad 128 makes contact with the surface of the patient's skin, the lever 170 is rotated through the fully retracted position, approximately as illustrated in FIG. 13, and the foot 141 and foot 152 apply pressure to the exposed adhesive portions of the tape portion 129' to adhere the tape portion 129' to the patient's skin.

While the tape portion 129' and dressing pad 128 are being applied to the patient's skin, a second tape portion 129' and dressing pad 128 are being staged for application, as illustrated most clearly in FIGS. 11-13.

Figure 14:
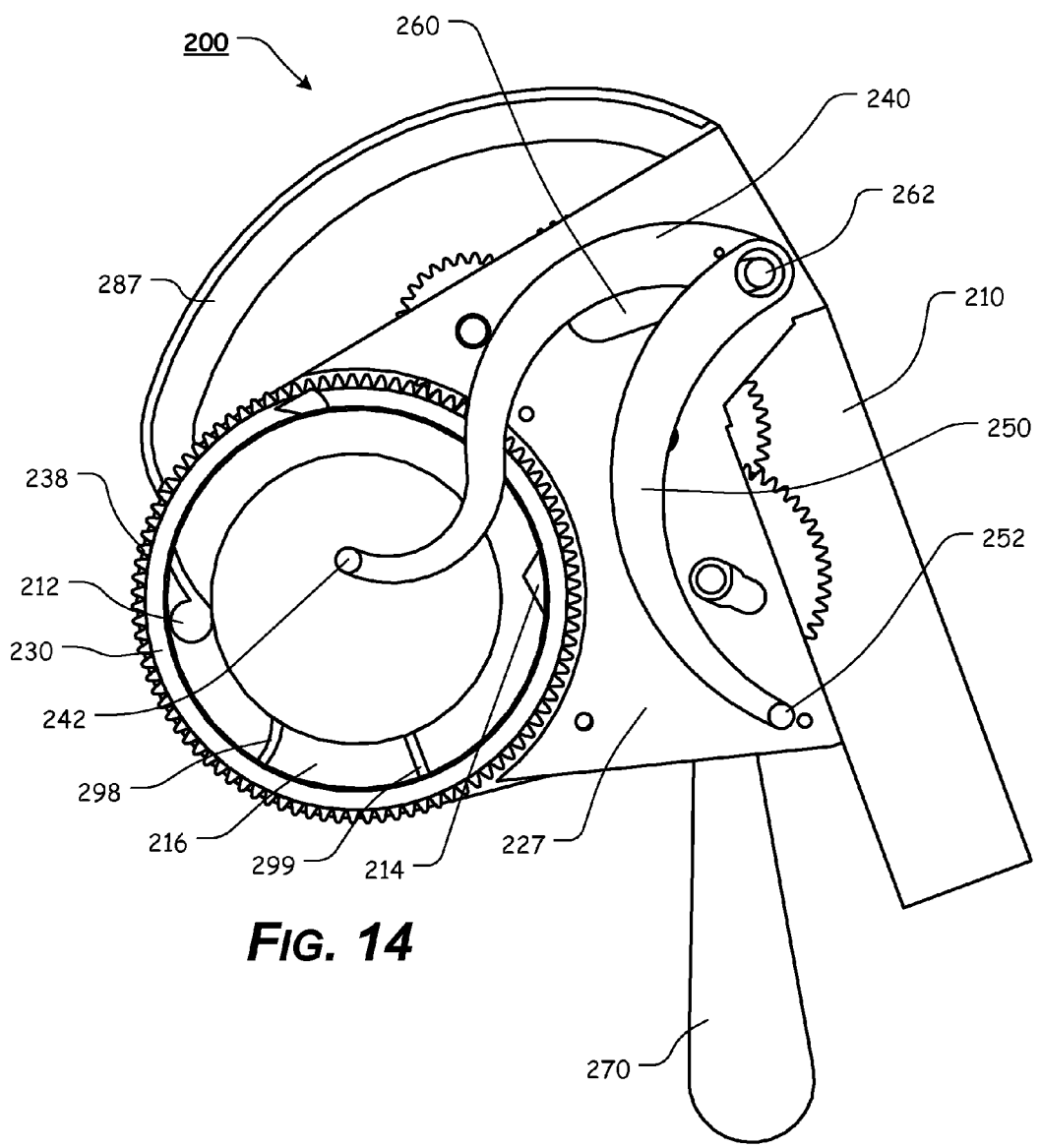
FIG. 14 illustrates a right side view of a second exemplary embodiment of a dressing applicator according to this invention.

FIG. 14 illustrates a right side view of a second exemplary embodiment 200, according to this invention. As shown in FIG. 14, the dressing applicator 200 comprises at least some of a frame 210, having frame apertures 211, a roller 212, a cutting element 214, a driver attachment ring 216, a roll attachment ring 218, a cover element 227 having cover element apertures 228, a driver wheel 230 having a driver arm 232 and a driver wheel gear 238, a first arm 240 having an aperture 241 and a foot 242, a second arm 250 having an aperture 251 and a foot 252, a swing arm 260 having an extension axle 262 and a keyed axle 264, a lever 270 having a lever axle 279, a gear system comprising a gear 271, a gear 272, a gear 273, a gear 274, a gear 275, a gear 276, and a gear 277, a keyed axle 280, and a keyed axle 281.

It should be understood that each of these elements corresponds to and operates similarly to the frame 110, having frame apertures 111, the roller 112, the cutting element 114, the driver attachment ring 116, the roll attachment ring 118, the cover element 127 having cover element apertures 126, the driver wheel 130 having the driver arm 132 and the driver wheel gear 138, the first arm 140 having the aperture 141 and the foot 142, the second arm 150 having the aperture 151 and the foot 152, the swing arm 160 having the extension axle 162 and the keyed axle 164, the lever 170 having the lever axle 179, the gear system comprising the gear 171, the gear 172, the gear 173, the gear 174, the gear 175, the gear 176, and the gear 177, the keyed axle 180, and the keyed axle 181, as described above with reference to the dressing applicator 100 of FIGS. 1-13.

However, as shown in FIG. 14, the handle/magazine and handle/magazine spring are removable and are shown as being removed from the dressing applicator 200.

Additionally, a protective arch 287 is included to provide additional protection to the first arm 240, second arm 250, and certain components of the gear system.

As shown in FIG. 14, the dressing applicator 200 also includes a first guide element 298 and a second guide element 299, each of which extends from the driver attachment ring 216 to provide additional guidance and/or support to the first arm 240 and the second arm 250.

Figure 15:
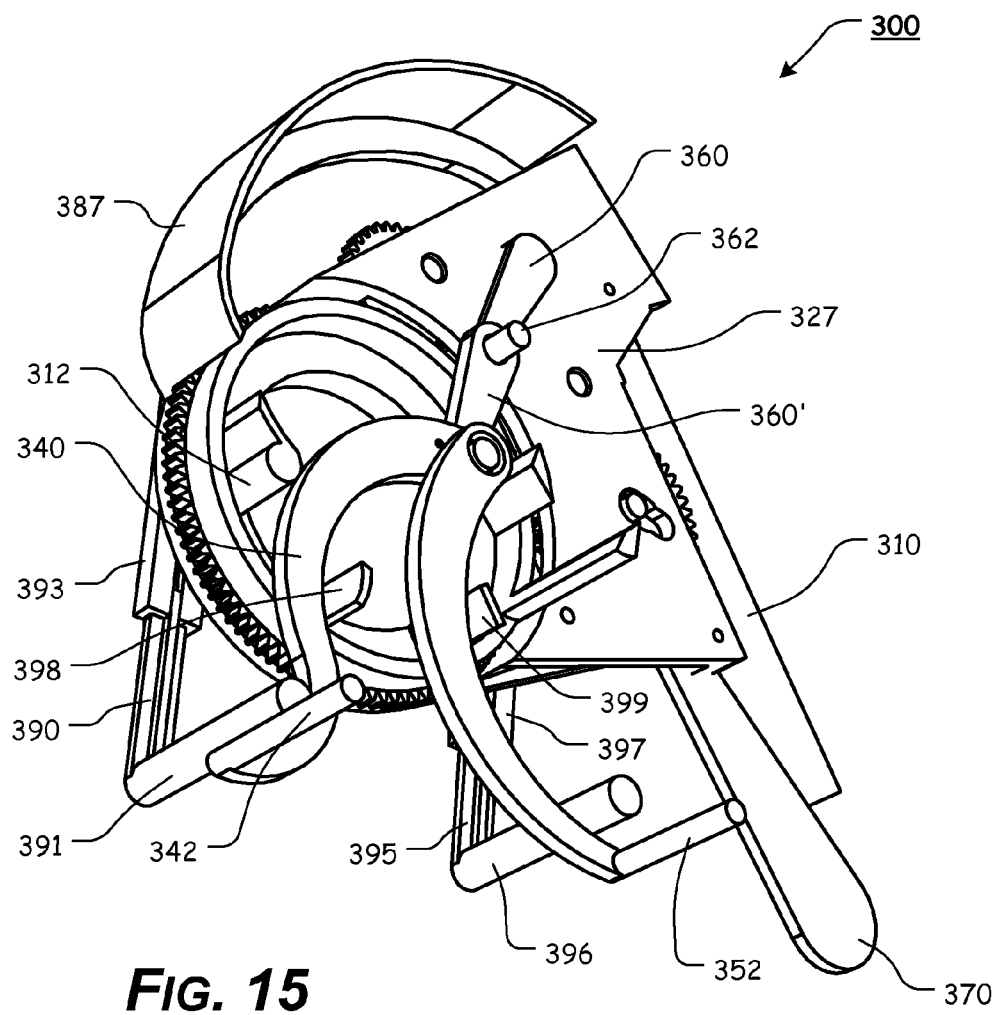
FIG. 15 illustrates a lower, perspective view of a third exemplary embodiment of a dressing applicator according to this invention.
Figure 16:
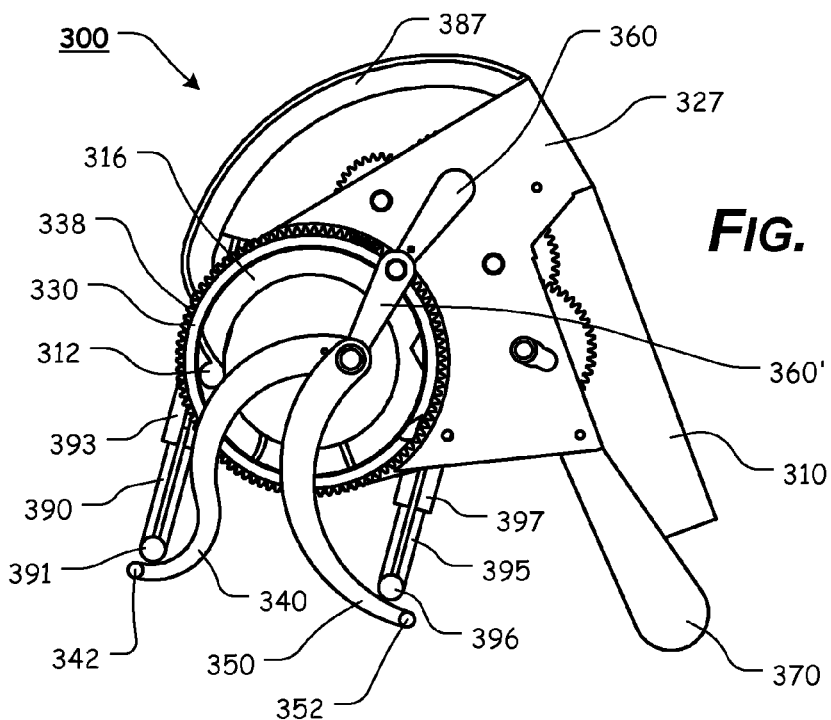
FIG. 16 illustrates a right side view of a third exemplary embodiment of a dressing applicator according to this invention.
Figure 17:
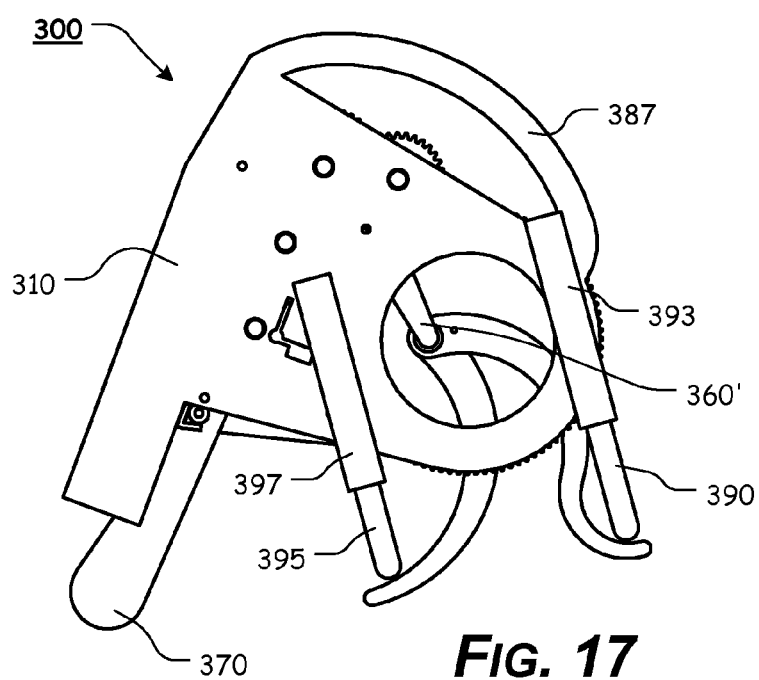
FIG. 17 illustrates a left side view of a third exemplary embodiment of a dressing applicator according to this invention.

FIGS. 15-17 illustrate a third exemplary embodiment of a dressing applicator 300 according to this invention. As shown in FIGS. 15-17, the dressing applicator 300 comprises at least some of a frame 310, having frame apertures 311, a roller 312, a cutting element 314, a driver attachment ring 316, a roll attachment ring 318, a cover element 327 having cover element apertures 328, a driver wheel 330 having a driver arm 332 and a driver wheel gear 338, a first arm 340 having an aperture 341 and a foot 342, a second arm 350 having an aperture 351 and a foot 352, a swing arm 360 having an extension axle 362 and a keyed axle 364, a lever 370 having a lever axle 379, a gear system comprising a gear 371, a gear 372, a gear 373, a gear 374, a gear 375, a gear 376, and a gear 377, a keyed axle 380, and a keyed axle 381.

It should be understood that each of these elements corresponds to and operates similarly to the frame 110, having frame apertures 111, the roller 112, the cutting element 114, the driver attachment ring 116, the roll attachment ring 118, the cover element 127 having cover element apertures 126, the driver wheel 130 having the driver arm 132 and the driver wheel gear 138, the first arm 140 having the aperture 141 and the foot 142, the second arm 150 having the aperture 151 and the foot 152, the swing arm 160 having the extension axle 162 and the keyed axle 164, the lever 170 having the lever axle 179, the gear system comprising the gear 171, the gear 172, the gear 173, the gear 174, the gear 175, the gear 176, and the gear 177, the keyed axle 180, and the keyed axle 181, as described above with reference to the dressing applicator 100 of FIGS. 1-13.

However, as shown in FIGS. 15-17, the handle/magazine and handle/magazine spring are removable and are shown as being removed from the dressing applicator 300.

Additionally, a protective arch 387 is included to provide additional protection to the first arm 340, second arm 350, and certain components of the gear system.

Furthermore, in order to increase the distance between the dressing applicator 300 and an application surface, an additional swing arm 360' is optionally added to the existing swing arm 360. As illustrated, the additional swing arm 360' extends out as the swing arm 360 is rotated to increase the distance that the first arm 340 and a second arm 350 extend.

In order to maintain the same tape portion 129' length while increasing the surface applicator extender arm 390, having an extender arm roller 391, and extender arm 395, having an extender arm roller 396 could be added with tracks 393 and 397 that telescope out when the tape portion 129' is caught on them and retracts through extension springs (not shown) when the tape portion 129' is fully deposited.

As shown in FIGS. 15-17, the dressing applicator 300 also includes a first guide element 398 and a second guide element 399, each of which extends from the driver attachment ring 316 to provide additional guidance and/or support to the first arm 340 and the second arm 350.

While this invention has been described in conjunction with the exemplary embodiments outlined above, the foregoing description of exemplary embodiments of the invention, as set forth above, are intended to be illustrative, not limiting and the fundamental invention should not be considered to be necessarily so constrained. It is evident that the invention is not limited to the particular variation set forth and many alternatives, adaptations modifications, and/or variations will be apparent to those skilled in the art.

It is to be understood that the phraseology of terminology employed herein is for the purpose of description and not of limitation. Unless defined otherwise, all technical and scientific terms used herein have the same meaning as commonly understood by one of ordinary skill in the art to which this invention belongs.

In addition, it is contemplated that any optional feature of the inventive variations described herein may be set forth and claimed independently, or in combination with any one or more of the features described herein.

Accordingly, the foregoing description of exemplary embodiments will reveal the general nature of the invention, such that others may, by applying current knowledge, change, vary, modify, and/or adapt these exemplary, non-limiting embodiments for various applications without departing from the spirit and scope of the invention and elements or methods similar or equivalent to those described herein can be used in practicing the present invention. Any and all such changes, variations, modifications, and/or adaptations should and are intended to be comprehended within the meaning and range of equivalents of the disclosed exemplary embodiments and may be substituted without departing from the true spirit and scope of the invention.

Also, it is noted that as used herein and in the appended claims, the singular forms "a", "and", "said", and "the" include plural referents unless the context clearly dictates otherwise. Conversely, it is contemplated that the claims may be so-drafted to require singular elements or exclude any optional element indicated to be so here in the text or drawings. This statement is intended to serve as antecedent basis for use of such exclusive terminology as "solely", "only", and the like in connection with the recitation of claim elements or the use of a "negative" claim limitation(s).

What is claimed is:

1. A dressing applicator, comprising:
   a frame comprising a substantially rigid portion of material having a substantially planar surface portion and including a driver attachment ring spaced apart from a roll attachment ring;
   a handle magazine, wherein the handle magazine is formed so as to allow one or more dressing pads to be at least partially contained within a cavity of the handle magazine, wherein the handle magazine includes an opening formed proximate a top end of the handle magazine, which allows the one or more dressing pads to be slidably removed from the cavity of the handle magazine, and wherein a handle magazine spring is positioned within the cavity of the handle magazine so as to provide a spring biasing force to the one or more dressing pads contained within the cavity of the handle magazine, biasing the one or more dressing pads toward the opening;
   a roller extending from the driver attachment ring;
   a cutting element extending from the driver attachment ring;
   a driver wheel, wherein a driver wheel gear is formed around an outer surface of the driver wheel, wherein the driver wheel is rotationally attached about an outer surface of the driver attachment ring, and wherein a driver arm extends from the driver wheel;
   a first arm, wherein the first arm comprises an elongate portion of material having a substantially recurved shape, wherein the first arm includes an aperture formed therethrough, proximate a first end of the first arm, and wherein a first arm foot extends proximate a second end of the first arm;

a second arm, wherein the second arm comprises an elongate portion of material having a substantially arcuate shape, wherein the second arm includes an aperture formed therethrough, proximate a first end of the second arm, and wherein a second arm foot extends proximate a second end of the second arm;

a swing arm, wherein the swing arm extends from a first end to a second end, wherein the swing arm includes an extension axle extending from a first side of the swing arm and a swing arm keyed axle extending from a second side of the swing arm, and wherein the extension axle is formed so as to be received within the aperture formed in the first arm and the aperture formed in the second arm and provide a pivot point for the first arm and the second arm, such that when the swing arm is rotated, the first arm and the second arm move from a retracted position to an extended position;

a lever, wherein the lever comprises an elongate portion of material having a longitudinal axis, wherein a lever axle extends perpendicular to the longitudinal axis of the lever and provides a point for the lever, such that the lever is pivotable between a fully extended position and a fully retracted position;

a gear system, wherein the gear system, in response to rotation of the lever rotates the driver wheel gear and the swing arm; and a cover element that covers the gear system and provides cover element apertures to maintain the gear system in place.

2. The dressing applicator of claim 1, wherein the driver attachment ring extends outwardly, substantially perpendicular, from the planar surface portion of the frame.

3. The dressing applicator of claim 1, wherein the roll attachment ring extends outwardly, substantially perpendicular, from the planar surface portion of the frame.

4. The dressing applicator of claim 1, wherein a longitudinal axis of the roller extends perpendicular to the planar surface portion of the frame.

5. The dressing applicator of claim 1, wherein the cutting element is a razor.

6. The dressing applicator of claim 1, wherein a longitudinal axis of the cutting element extends perpendicular to the planar surface portion of the frame.

7. The dressing applicator of claim 1, wherein the roller and the cutting element are positioned at opposing sides of the driver attachment ring.

8. The dressing applicator of claim 1, wherein the driver arm extends from the driver wheel so as to interact with the cutting element when the driver wheel is rotated about the driver attachment ring.

9. The dressing applicator of claim 1, wherein the gear system increases rotational input from the lever to 360 degrees at the swing arm and at the driver wheel.

10. A dressing applicator, comprising:
a frame having a substantially planar surface portion and including a driver attachment ring spaced apart from a roll attachment ring;

a handle magazine, wherein the handle magazine is formed so as to allow one or more dressing pads to be at least partially contained within a cavity of the handle magazine, and wherein the handle magazine includes an opening formed proximate a top end of the handle magazine, which allows the one or more dressing pads to be slidably removed from the cavity of the handle magazine;

a roller extending from the driver attachment ring;

a cutting element extending from the driver attachment ring;

a driver wheel, wherein a driver wheel gear is formed around an outer surface of the driver wheel, wherein the driver wheel is rotationally attached about an outer surface of the driver attachment ring, and wherein a driver arm extends from the driver wheel;

a first arm, wherein the first arm comprises an elongate portion of material, wherein the first arm includes an aperture formed therethrough proximate a first end of the first arm, and wherein a first arm foot extends proximate a second end of the first arm;

a second arm, wherein the second arm comprises an elongate portion of material, wherein the second arm includes an aperture formed therethrough proximate a first end of the second arm, and wherein a second arm foot extends proximate a second end of the second arm;

a swing arm, wherein the swing arm extends from a first end to a second end and includes an extension axle extending from a first side of the swing arm and a swing arm keyed axle extending from a second side of the swing arm, and wherein the extension axle is formed so as to be received within the aperture formed in the first arm and the aperture formed in the second arm and provide a pivot point for the first arm and the second arm, such that when the swing arm is rotated, the first arm and the second arm move from a retracted position to an extended position;

a lever having a longitudinal axis, wherein a lever axle extends from the lever perpendicular to the longitudinal axis of the lever and provides a point for the lever, such that the lever is pivotable between a fully extended position and a fully retracted position;

a gear system, wherein the gear system, in response to rotation of the lever rotates the driver wheel gear and the swing arm; and a cover element, wherein the cover element includes cover element apertures to maintain the gear system in place and the frame includes frame element apertures to maintain the gear system in place.

11. The dressing applicator of claim 10, wherein the first arm has a substantially recurved shape.

12. The dressing applicator of claim 10, wherein the second arm has a substantially arcuate shape.

13. The dressing applicator of claim 10, wherein the driver attachment ring extends outwardly, substantially perpendicular, from the planar surface portion of the frame.

14. The dressing applicator of claim 10, wherein the roll attachment ring extends outwardly, substantially perpendicular, from the planar surface portion of the frame.

15. The dressing applicator of claim 10, wherein a longitudinal axis of the roller extends perpendicular to the planar surface portion of the frame.

16. The dressing applicator of claim 10, wherein a longitudinal axis of the cutting element extends perpendicular to the planar surface portion of the frame.

17. The dressing applicator of claim 10, wherein the driver arm extends from the driver wheel so as to interact with the cutting element when the driver wheel is rotated about the driver attachment ring.

18. The dressing applicator of claim 10, wherein the gear system increases rotational input from the lever to 360 degrees at the swing arm and at the driver wheel.

19. A method for applying a tape portion of a tape roll and a dressing pad to a surface, comprising:
- providing a dressing applicator, wherein the dressing applicator comprises;
- a frame having a substantially planar surface portion and including a driver attachment ring spaced apart from a roll attachment ring;
- a handle magazine, wherein the handle magazine is formed so as to allow the dressing pad to be at least partially contained within a cavity of the handle magazine, and wherein the handle magazine includes an opening formed proximate a top end of the handle magazine, which allows the dressing pad to be slidably removed from the cavity of the handle magazine;
- a roller extending from the driver attachment ring;
- a cutting element extending from the driver attachment ring;
- a driver wheel, wherein a driver wheel gear is formed around an outer surface of the driver wheel, wherein the driver wheel is rotationally attached about an outer surface of the driver attachment ring, and wherein a driver arm extends from the driver wheel;
- a first arm, wherein the first arm comprises an elongate portion of material, wherein the first arm includes an aperture formed therethrough proximate a first end of the first arm, and wherein a first arm foot extends proximate a second end of the first arm;
- a second arm, wherein the second arm comprises an elongate portion of material, wherein the second arm includes an aperture formed therethrough proximate a first end of the second arm, and wherein a second arm foot extends proximate a second end of the second arm;
- a swing arm, wherein the swing arm extends from a first end to a second end and includes an extension axle extending from a first side of the swing arm and a swing arm keyed axle extending from a second side of the swing arm, and wherein the extension axle is formed so as to be received within the aperture formed in the first arm and the aperture formed in the second arm and provide a pivot point for the first arm and the second arm, such that when the swing arm is rotated, the first arm and the second arm move from a retracted position to an extended position;
- a lever having a longitudinal axis, wherein a lever axle extends from the lever perpendicular to the longitudinal axis of the lever and provides a point for the lever, such that the lever is pivotable between a fully extended position and a fully retracted position;
- a gear system, wherein the gear system, in response to rotation of the lever rotates the driver wheel gear and the swing arm; and
- a cover element, wherein the cover element includes cover element apertures to maintain the gear system in place and the frame includes frame element apertures to maintain the gear system in place;

wherein the method comprises:

supplying the tape roll on the roll attachment ring;

supplying the dressing pad in the cavity of the handle magazine;

rotating the lever so that the dressing pad is applied to the tape portion of the tape roll;

positioning the dressing pad above the surface;

continuing to rotate the lever such that the dressing pad makes contact with the surface and the tape portion is released from the roller and cutting element; and continuing to rotate the lever such that the first arm foot and second arm foot apply pressure to exposed adhesive portions of the tape portion to adhere the tape portion to the surface.

* * * * *